United States Patent [19]

Niwa et al.

[11] Patent Number: 5,480,804
[45] Date of Patent: Jan. 2, 1996

[54] METHOD OF AND APPARATUS FOR DETECTING MICROORGANISMS

[75] Inventors: Motohiro Niwa; Tetsuji Yasui, both of Tokyo; Takahiro Ode, Yokohama, all of Japan

[73] Assignee: Kirin Beverage Corporation, Tokyo, Japan

[21] Appl. No.: 47,606

[22] Filed: Apr. 13, 1993

Related U.S. Application Data

[63] Continuation-in-part of Ser. No. 546,097, Jun. 27, 1990, abandoned.

[30] Foreign Application Priority Data

Jun. 28, 1989 [JP] Japan .................. 1-165635
Nov. 10, 1989 [JP] Japan .................. 1-292998

[51] Int. Cl.⁶ ........................ C12M 1/34
[52] U.S. Cl. .................. 435/286.1; 435/808; 435/288.7; 435/287.1; 422/82.08; 250/461.2
[58] Field of Search ................ 435/29, 30, 34, 435/284, 291, 808; 422/82.05, 82.08; 356/36, 38, 337, 338, 341, 343; 250/458.1–462.1

[56] References Cited

U.S. PATENT DOCUMENTS

| | | | |
|---|---|---|---|
| 3,916,205 | 10/1975 | Kleinerman | 250/461 |
| 4,125,828 | 11/1978 | Resnick | 382/6 |
| 4,127,773 | 11/1978 | West | 250/461 R |
| 4,354,114 | 10/1982 | Karnaukhov et al. | 250/458.1 |
| 4,499,052 | 2/1985 | Fulwyler | 422/52 |
| 4,745,285 | 5/1988 | Recktenwald et al. | 250/458.1 |
| 4,900,934 | 2/1990 | Peeters et al. | 250/461.2 |

FOREIGN PATENT DOCUMENTS 60-80745 5/1985 Japan.
61-20839 1/1986 Japan.

OTHER PUBLICATIONS

J Applied Bacteriology. 1982, vol. 53, 323–329.

*Primary Examiner*—William H. Beisner
*Attorney, Agent, or Firm*—Ladas & Parry

[57] ABSTRACT

A microorganism detecting apparatus comprising a fluorescence microscope section which is furnished with a motor-driven stage for placing thereon a microorganism sample subjected to fluorescent staining, and a light source portion for projecting excitation light of predetermined wavelength on the sample; a detection section which detects and photoelectrically converts fluorescence of specified wavelength from the microorganism sample at a position posterior to the microscope section; a filter unit which limits the band of frequencies ascribable to noise in relation to an electric signal from the detection section; a signal processor which reads the output value of the band-limited signal from the detection section, and which processes the read output value; and an automatic inspection section which drives the stage so as to permit the microorganism sample to be scanned over its whole area, and which stores each signal detection part in the sample so as to permit a fluorescent substance at the part to be verified.

8 Claims, 10 Drawing Sheets

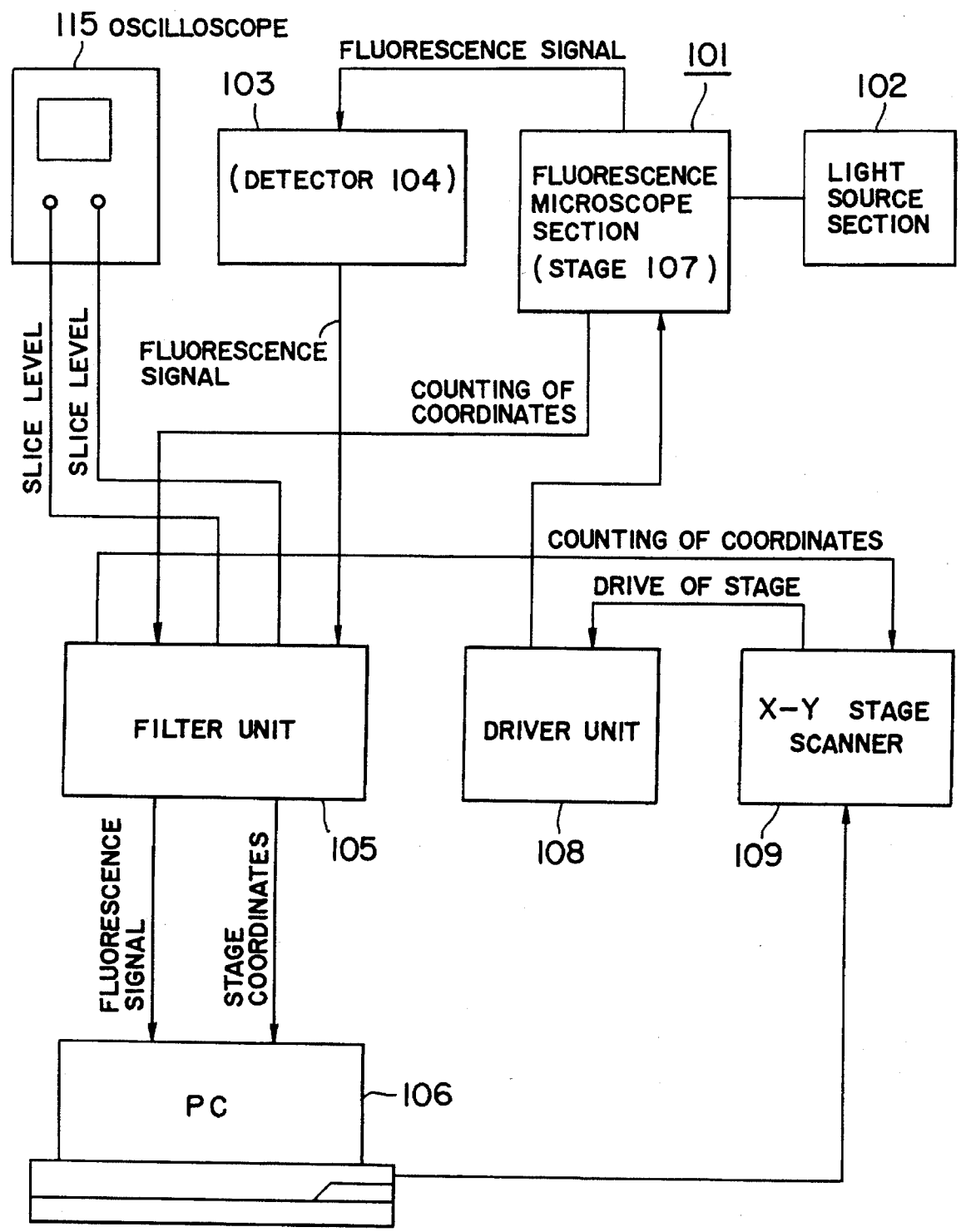
F I G. 1

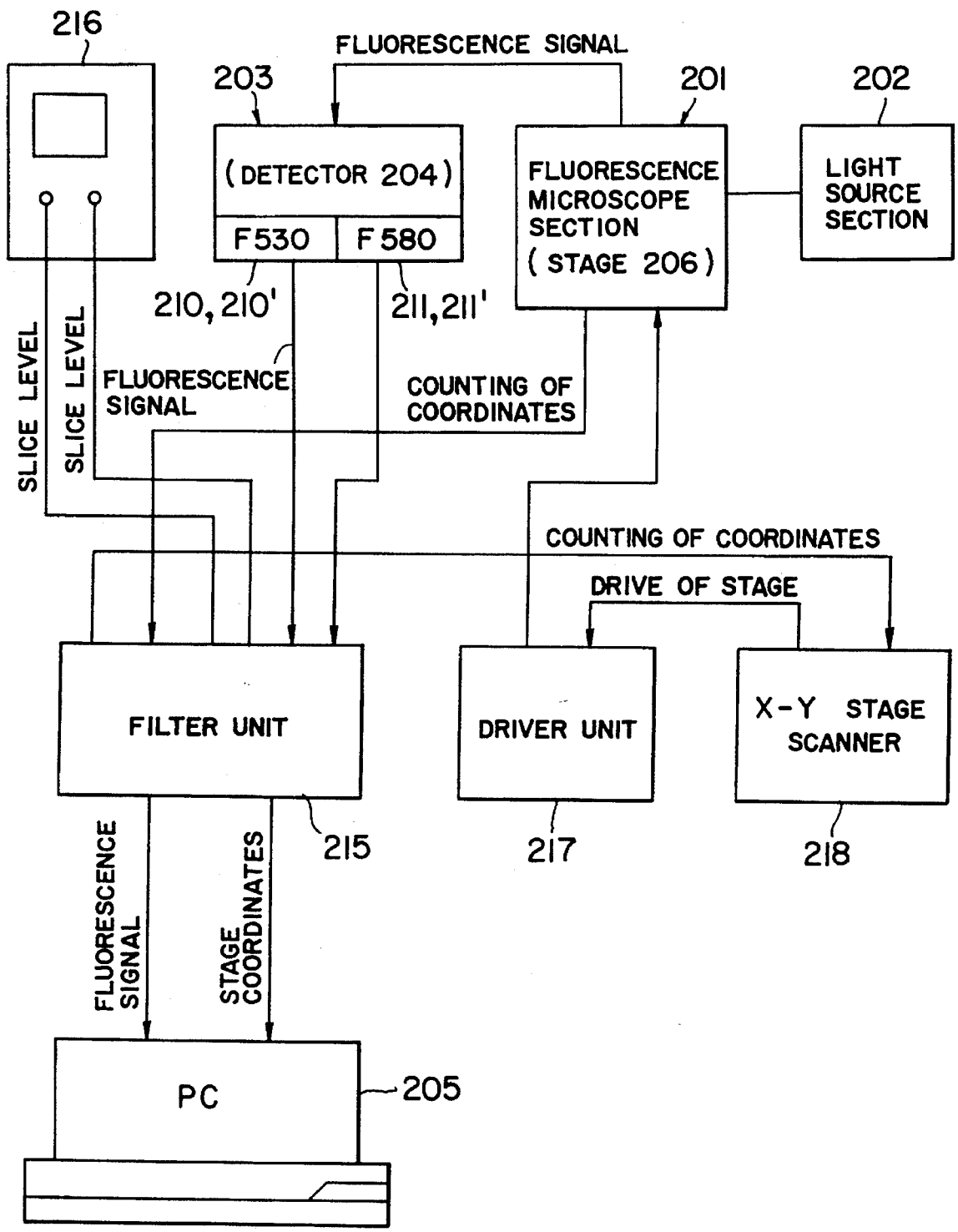
F I G. 7

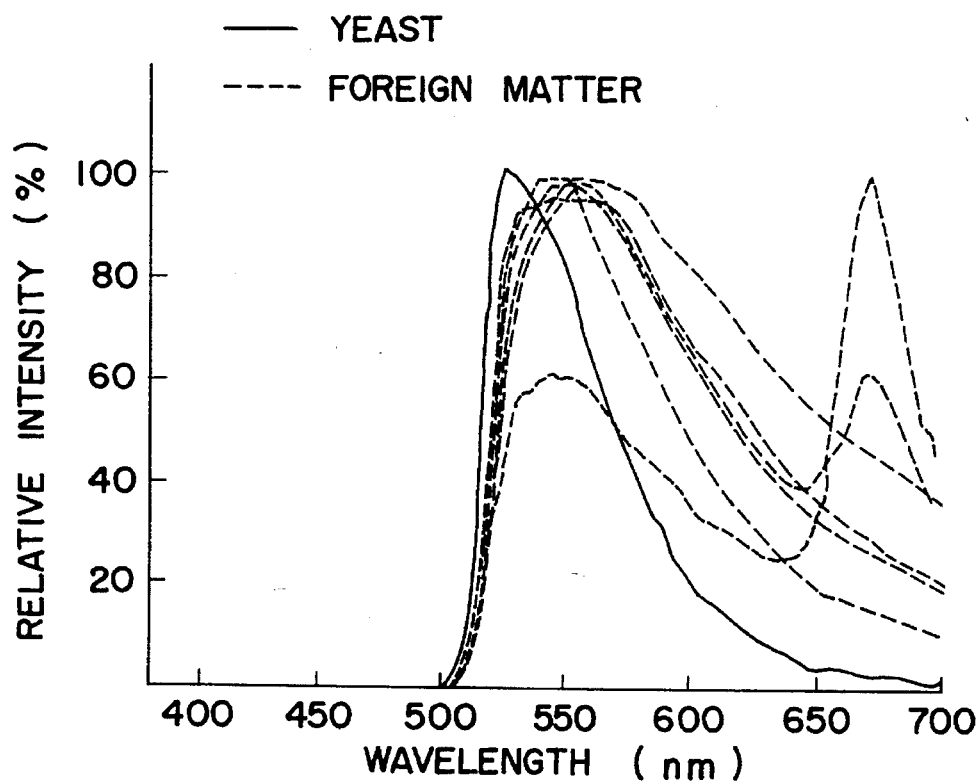
F I G. 11
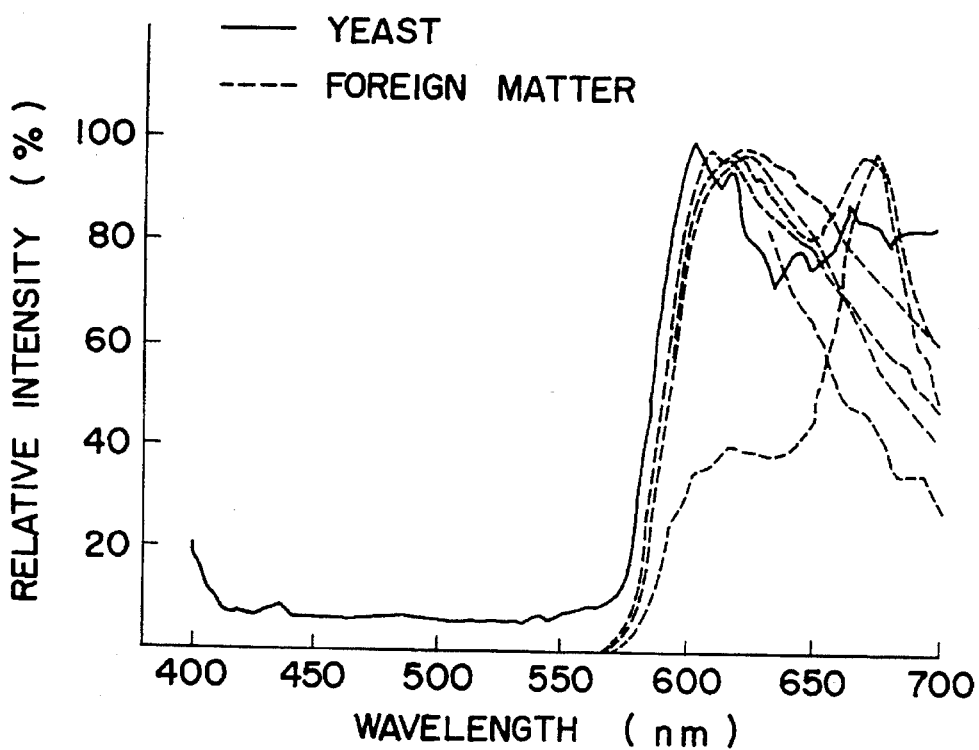
F I G. 12

METHOD OF AND APPARATUS FOR DETECTING MICROORGANISMS

This is a continuation-in-part of application Ser. No. 07/546,097 filed on Jun. 27, 1990 now abandoned.

BACKGROUND OF THE INVENTION

(1) Field of the Invention

The present invention relates to a method of and apparatus for detecting microorganisms. More particularly, it relates to a microorganism detecting method and apparatus for measuring microorganisms contained in a microorganism sample such as a sample in which the microorganisms of an object to-be-inspected are caught on a membrane filter and then subjected to fluorescent staining.

(2) Description of the Related Art

Heretofore, microbial tests in, for example, the manufacturing process managements and product quality controls of drinkables such as beer, edibles, pharmaceuticals, cosmetics etc. have been conducted in accordance with cultural tests requiring multifarious culture grounds, and long days have been expended till the ends of the tests. Therefore, test results such as the presence of microorganisms and the numbers of microorganisms have been known late, and there have been many limitations at the stages of researches, developments, manufactures and product shipments in various fields.

In view of such circumstances, a large number of rapid measurement methods have heretofore been devised (Misao HARUTA, et al., Simplification, Automation and Speed-up of Food-microbiological Tests, p. 11, Science Forum (1985), and Toshiki MORICHI, New Food Industry, 30, 49 (1989)), but satisfactory methods or apparatuses have not been developed yet. There have been developed, for example, an ATP measurement method (Molin, Ö., Milsson, L. and Ånséhn, S., J. Clin. Microbiol., 18, 521 (1983)), an impedance method (Brown, D., Warner, M., Taylor, C. and Warren, R., J. Clin. Pathol., 37, 65–69 (1984)), an enzyme/fluorescence detecting method (Japanese Patent Laid-open Pub. No. 116700/1983), and a DEFT method in which a membrane filter method and a fluorescence microscope method are combined (G. L. PETTIPHER, UBALDINAM and RODRIGUES, J. Appl. Bacteriol., 53, 323 (1982)), and apparatuses to which these principles are applied are commercially available. However, problems are still left in points of accuracy and rapidity. More specifically, the rapid measurement methods presently in practical use exhibit, at the utmost, accuracies of $10^2$–$10^4$ microorganisms/ml. One day is usually required for one microorganism to reach this germ density. Another difficulty is that the running costs of culture grounds, reagents etc. are high.

Recently, an apparatus wherein microorganisms are automatically detected rapidly by a fluorescence detecting method subjecting the microorganisms to fluorescent staining has been proposed (Japanese Patent Laid-open Pub. No. 53447/1988), and it is studied to put the apparatus into practical use as ones of higher rapidity. Since, however, microscopic foreign matters having auto-fluorecences exist in large numbers in the natural world, the apparatuses simultaneously detect the auto-fluorescent foreign matters other than the fluorescent-stained microorganisms. Consequently, in the test of microorganisms contained in a sample to-be-inspected, for example, a product such as beer or any other drink, there is left the problem that the final decision cannot held being relied on a verification based on a visual inspection with a fluorescence microscope section. Accordingly, it is the most important theme to solve the problem in the automation of the microorganism detection based on the fluorescence detecting method.

SUMMARY OF THE INVENTION

The present invention has for its object to solve the problems mentioned above, and is intended to provide a microorganism detecting apparatus in a first aspect accomplishing the object in such a way that a fluorescence microscope and a fluorescence measuring device are combined, while the noise of electric signals from a detector is reduced, and that the scanning of a microorganism sample is automated, while the data processing of signal measurement values and the verification of the signal detection positions of the microorganism sample can be automated.

More specifically, the microorganism detecting apparatus according to the first aspect of the present invention comprises a fluorescence microscope section which is furnished with a motor-driven stage for placing thereon a microorganism sample subjected to fluorescent staining, and light source means for projecting excitation light of predetermined wavelength on the sample; detection means for detecting and photoelectrically converting fluorescence of specified wavelength from the microorganism sample at a position posterior to said microscope section; means for limiting a band of frequencies ascribable to noise in relation to an electric signal from said detection means; signal processing means for reading an output value of the band-limited signal from said detection means and processing the read signal output value; and automatic inspection means for driving said stage so as to permit the microorganism sample to be scanned over its whole area, and for storing each signal detection part in the sample so as to permit a fluorescent substance at the part to be verified.

Further, the present invention has for its object to realize the optical discrimination between fluorescent-stained microorganisms and any auto-fluorescent foreign matter, and it is intended to provide a microorganism detecting method and apparatus in a second aspect accomplishing the object by utilizing a discrepancy in values selected from the group consisting of the spectra, intensities, intensity differences, intensity ratios, and intensity ratio differences of fluorescences which are emitted in accordance with excitation light of specified condition.

More specifically, the microorganism detecting method according to the second aspect of the present invention is a method of detecting microorganisms wherein the microorganisms contained in a microorganism sample subjected to fluorescent staining are sensed by microphotometry; characterized by comprising the step of measuring fluorescences emitted by projecting excitation light of at least one wavelength on the microorganism sample, and the step of discriminating the fluorescent-stained microorganisms and any auto-fluorescent foreign matter by utilizing a discrepancy in obtained values selected from the group consisting of spectra, intensities, intensity differences, intensity ratios, and intensity ratio differences of the fluorescences.

Besides, the microorganism detecting apparatus according to the second aspect of the present invention is an apparatus for detecting microorganisms having microphotometric means for sensing the microorganisms contained in a microorganism sample subjected to fluorescent staining; characterized by comprising light-source projection means for projecting excitation light of at least one wavelength on the microorganism sample, detection means for detecting and photoelectrically converting fluorescences emitted from the microorganism sample, and signal processing means for reading output values of signals from said detection means so as to find values selected from the group consisting of spectra, intensities, intensity differences, intensity ratios, and intensity ratio differences of the fluorescences, and for measuring the fluorescent-stained microorganisms in discrimination from any auto-fluorescent foreign matter on the basis of a discrepancy in the found values.

With the microorganism detecting apparatus in the first aspect of the present invention, first of all, the fluorescent-stained microorganism sample is placed on the stage of the fluorescence microscope section, and the light from the light source is projected on the microorganism sample. Then, the fluorescence is radiated from the microorganism sample. After passing through the microscope section, the fluorescence has its component of specified wavelength sensed and converted into the electric signal by the detection means. The signal is passed through the means for limiting the band of frequencies ascribable to noise in relation to the electric signal from the detection means, thereby to have its frequency band limited and to have its current in the frequency band ascribable to the noise attenuated, whereby the noise of the signal is reduced. Owing to the microphotometry capable of measuring a very small area, and the reduction of the noise, the individual microorganisms are accurately detected, and the radiated fluorescence is reliably detected as the electric signal even when it has a low intensity due to a small number of microorganisms contained in the sample.

The electric signal from the detection means as having undergone the limitation of the frequency band is read and processed by the signal processing means, whereby a fluorescent substance is measured. As to the measurement data thus obtained, the signal detection part in the microorganism sample is verified by the automatic inspection means. Using the microscopic image of this part, the microorganisms are discriminated from any other fluorescent substance, and unnecessary data is deleted.

Owing to the signal processing means and the automatic inspection means, there are automatically performed the steps of the microorganism measurement as described above, that is, such steps as the scanning of the microorganism sample over the whole area, the measurement of the fluorescence from the microorganism sample, the processing of the data based on the measurement, and the verification of the signal detection position.

With the microorganism detecting method in the second aspect of the present invention, first of all, in sensing the fluorescent-stained microorganism sample by the microphotometry, the microorganism sample is irradiated with the excitation light of one wavelength or is successively irradiated with the excitation lights of two or more wavelengths. Then, fluorescences are emitted from the sample. Subsequently, the spectrum of each fluorescence and the intensity thereof at a specified wavelength are measured, and the value selected from the group consisting of the intensity difference, intensity ratio and intensity ratio difference of each fluorescence is found as may be needed.

Data items which are based on any one value among the fluorescence spectrum and the intensity, intensity difference, intensity ratio and intensity ratio difference of the fluorescence or on the combination of a plurality of values among them, differ between the fluorescent-stained microorganisms and any auto-fluorescent foreign matter. Therefore, a reference value for distinguishing the microorganisms and the foreign matter is set beforehand.

The values selected from the group consisting of the fluorescence spectra obtained fluorometrically and the intensities, intensity differences, intensity ratios and intensity ratio differences of the fluorescences are compared with the reference value, whereby the microorganisms in the sample are detected in discrimination from the auto-fluorescent foreign matter.

Accordingly, with the microorganism detecting apparatus in the second aspect of the present invention, first of all, the fluorescent-stained microorganisms are set at the predetermined position of the fluorescence microscope section, and they are irradiated with the excitation light of one wavelength or are successively irradiated with the excitation lights of two or more wavelengths. Then, fluorescences are emitted from the sample of the microorganisms.

The fluorescences of various wavelengths or specified wavelengths are sensed and converted into the electric signals by the detection means. Each of the electric signals is read and processed by the signal processing means, and the value selected from the group consisting of the spectrum, intensity, intensity difference, intensity ratio and intensity ratio difference of each fluorescence is found. Further, data which is based on any one value among the fluorescence spectrum and the intensity, intensity difference, intensity ratio and intensity ratio difference of the fluorescence or on the combination of a plurality of values among them is compared by the signal processing means with a reference value which is previously set for distinguishing the fluorescent-stained microorganisms and any auto-fluorescent foreign matter, whereby the microorganisms are detected in discrimination from the auto-fluorescent foreign matter.

BRIEF DESCRIPTION OF THE DRAWINGS

FIG. 1 is a block diagram for explaining the whole construction of a detecting or measuring apparatus of an embodiment according to the first aspect of the present invention.

FIG. 7 is an explanatory block diagram showing an example of the whole construction of the detecting apparatus in the second aspect of the present invention.

FIG. 11 shows discrepancies in the fluorescence spectra of the fluorescent-stained beer yeast and auto-fluorescent foreign matters in drinks on the market (black tea, oolong tea and ptisan) as based on B excitation light.

FIG. 12 shows discrepancies in the fluorescence spectra of the fluorescent-stained beer yeast and auto-fluorescent foreign matters in the drinks on the market (black tea, oolong tea and ptisan) as based on G excitation light.

DETAILED DESCRIPTION OF THE PREFERRED EMBODIMENTS

Detecting Apparatus in First Aspect

A microorganism detecting apparatus according to the first aspect of the present invention is an automatic inspection apparatus which has the construction as described before. It is the basic principle of the apparatus to measure microorganisms in such a way that (a) means for limiting the band of frequencies ascribable to noise in relation to an electric signal into which fluorescence from a very small area in a microorganism sample has been photoelectrically converted by detection means is used for limiting the band and reducing the noise of the signal, thereby to enhance the detection sensitivity of the apparatus, that (b) the electric signal from the detection means as subjected to the limitation of the frequency band is read and processed by signal processing means, thereby to measure the signal as a fluorescent substance, that (c) a signal detection part in the microorganism sample is verified as to the measurement data at the step (b) by automatic inspection means, thereby permitting the operator of the apparatus to discriminate the microorganisms of the sample from any other fluorescent substance with the microscopic image of this part, and that (d) the steps of the microorganism measurement are automatically carried out by the signal processing means and the automatic inspection means.

The fluorescent-stained microorganism sample for use in the measuring apparatus according to the present invention should preferably be one in which microorganisms in an object to-be-inspected, for example, a drink, water or air (concretely, a yeast in beer by way of example) are caught on a membrane filter having a suitable pore size and then stained with a fluorescent material (any of, for example, fluorescein diacetate, propidym iodide, fluorescein isothiocyanate, acridine orange, and ethidym bromide, among which the material fluorescein diacetate is favorable). If necessary, the microorganisms are cultured for a short time and then subjected to the staining.

Figure 2:
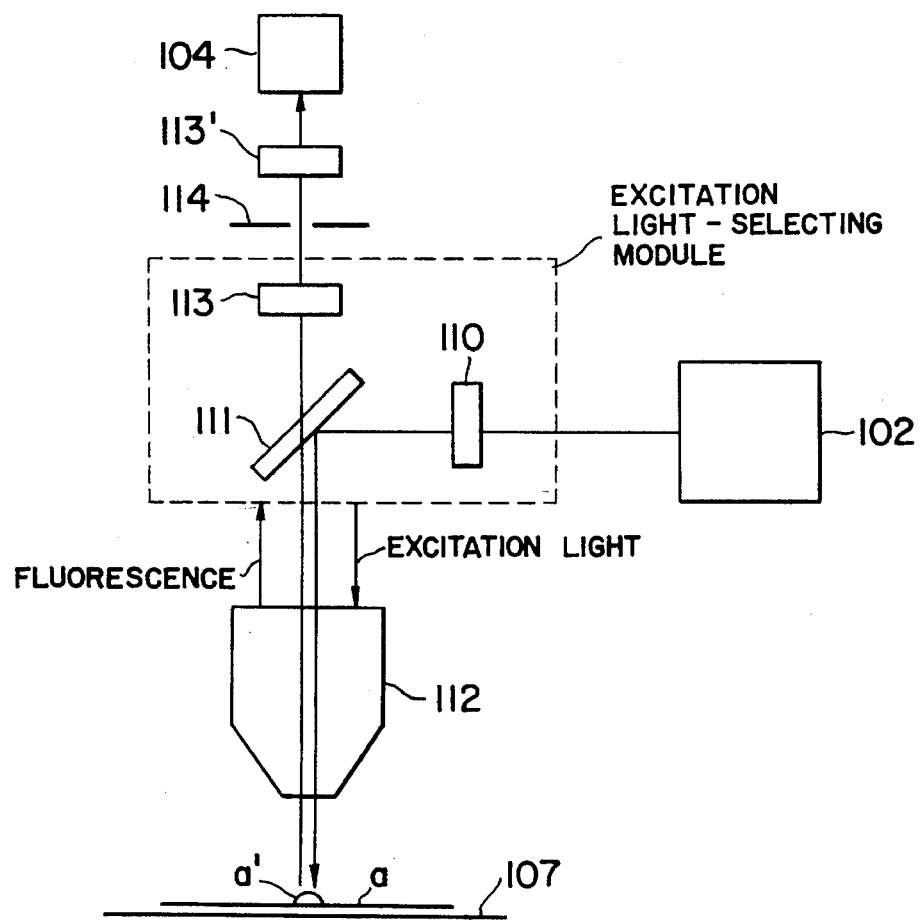
FIG. 2 is an explanatory diagram showing an example of the fundamental construction of a microphotometer section included in the measuring apparatus in FIG. 1.
Figure 3:
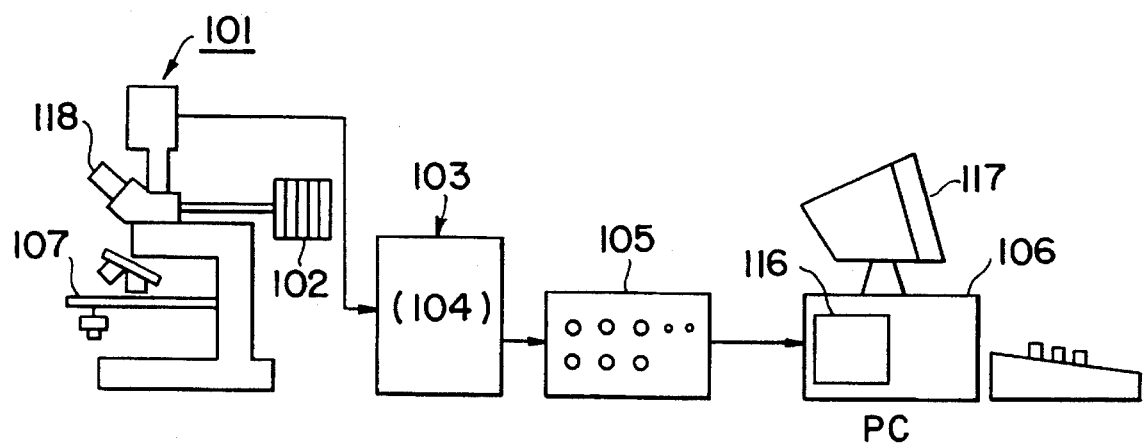
FIG. 3 is an explanatory diagram showing the flow of loading a microcomputer with the output value of fluorescence emitted from a sample in the detecting apparatus in the first aspect.

A preferred embodiment of the measuring apparatus according to the present invention is shown in FIGS. 1–3.

Now, the present invention will be more concretely described with reference to FIGS. 1–3.

The measuring apparatus comprises a fluorescence microscope section 101 which is furnished with a motor-driven stage 107 for placing thereon a microorganism sample a subjected to fluorescent staining, and light source means (including a light source unit 102) for projecting excitation light of predetermined wavelength on the sample a; a detection section 103 which detects and photoelectrically converts fluorescence of specified wavelength from the microorganism sample a at a position behind the microscope section 101, namely, a position optically downstream thereof; a signal filter unit 105 which serves as means for limiting the band of frequencies ascribable to noise in relation to an electric signal from the detection section 103; a microcomputer (PC) 106 which serves as signal processing means for reading and processing the output value of the band-limited signal from the detection section 103; and automatic inspection means constructed of the microcomputer 106, a driver unit 108 and an X-Y stage scanner 109, for driving the stage 107 thereby permitting the microorganism sample a to be scanned over its whole surface and also for storing a signal detection part in the sample a thereby permitting fluorescent substances at this part to be verified (refer to FIGS. 1 and 3).

The fluorescence microscope section 101, the light source section 102 and the detection section 103 construct a microfluorometer section, the major practicable constituents of which are shown in FIG. 2.

The microfluorometer section comprises the light source section 102 such as a mercury-arc lamp or xenon-arc lamp; the motor-driven stage 107 on which the microorganism sample a is placed; a filter 110 for selecting the excitation light, a dichroic mirror 111 and an objective 112 which are disposed in an optical path extending from the light source section 102 to the stage 107; filters 113 and 113' which serve to select the specified wavelength of the fluorescence that is emitted from the sample a by the projection of the excitation light from the light source section 102; a slit for a diaphragm 114 which is interposed between the filters 113 and 113'; and a detector 104 such as photomultiplier tube, photodiode or phototransistor, which detects and photoelectrically converts the fluorescence of the microorganism sample a having passed through the slit 114 as well as the filter 113' and which is preferably the photomultiplier tube.

The signal filter unit 105 is provided at a stage succeeding the microfluorometer section in terms of the electric signal, namely, a stage succeeding the detector 104. The filter unit 105 passes only a current of specified frequency band, and it can be formed of a band-limiting circuit arrangement which is generally employed in the fields of communications etc. The range of frequencies in the limited band is properly set depending upon the combination of conditions such as the scanning speed of the microorganism sample a, the magnifying power of the objective 112, and the slit width of the slit 114.

In the apparatus according to the present invention, an oscilloscope 115 for observing the variation of the waveform of the signal may well be comprised as shown in FIG. 1. It is desirable that the detection intensity of the signal from the signal filter unit 105 is set by the oscilloscope 115 so as to cut off signals lower than the predetermined intensity, whereby the microcomputer 106 to be described below is caused to read only the specified signal as desired.

The microcomputer 106 has the automatic fluorescence inspection function of automatically performing a process for measuring the microorganism sample a, and the signal processing function of reading the output value of the band-limited signal from the detector 104 and then processing the read output value.

The automatic fluorescence inspection function is fulfilled by the automatic fluorescence inspection program of the microcomputer 106. It includes the function of driving the stage 107 so that the whole surface of the microorganism sample a subjected to the fluorescent staining, for example, a microorganism sample in which microorganisms are caught on a membrane filter (having a diameter of, e.g., about 10–50 mm) and are subjected to the fluorescent staining can be scanned, and the function ("verify" function) of storing the signal detection part in the microorganism sample a so that the fluorescent substances at this part can be verified again by a microscopic observation after the sample has been scanned. While constructions having such functions may be any desired ones, the following preferable examples are mentioned:

In case of the former function, the sample placing stage 107 is driven through the driver unit 108 by the X-Y stage scanner 109 so as to control the positional movement thereof. In case of the latter function, the microcomputer 106 is caused by the driver unit 108 to read the movement magnitude of the motor-driven stage 107 and to load the fluorescent output detection part, namely, signal detection part in the microorganism sample a, thereby making it possible to verify the part by the visual microscopic observation after the scanning of the sample. Thus, the fluorescent substances at the detection part can be verified with a microscopic image so as to discriminate the microorganisms from the other fluorescent substances and to delete incorrect data.

On the other hand, the signal processing function includes the function of loading the fluorescent output value, the function of displaying inspection data, and the function of filing the inspection data.

The function of loading the fluorescent output value is such that the waveform of the electric signal from the detector 104 (or the detection section 103) having passed through the filter unit 105 is input to an A/D (analog-to-digital) conversion board 116 built in the microcomputer 106 so as to be A/D-converted, and that the maximum amplitude value of the resulting data is searched out and read as the fluorescent output value by the microcomputer 106 (refer to FIG. 3).

The function of displaying the inspection data consists of the mad display of the detection positions of the microorganisms a' on the fluorescent-stained microorganism sample a, the display of the histogram of detection numbers versus individual fluorescent intensities, the display of the total detection number, etc. (refer to FIG. 4).

The function of filing the inspection data makes it possible to file and store an automatically inspected result at the end of the inspection. Thus, the file can be drawn out and referred to under the management of the microcomputer 106 at will as may be needed.

As the function of the microcomputer 106, it is also possible to afford a function similar to the function which is based on the setting of the signal detection intensity by the oscilloscope 115, that is, the function of cutting off signals below a predetermined intensity from the signal filter unit 105.

The operation of the measuring apparatus according to the present invention is as explained in the following:

First, a microorganism sample a in which microorganisms in an object to-be-inspected (such as beer) are caught on a membrane filter and then subjected to fluorescent staining is prepared, and it is placed on the stage 107 of the fluorescence microscope section 101. In this case, actually the above microorganism sample is fixed on slide glass or the like, which is used as a sample for the inspection. Light emitted from the light source section 102 is passed through the filter 110 for selecting the entering excitation light and is further passed through the objective 112 via the dichroic mirror 111 as the excitation light of specified wavelength (for example, 490 nm if the staining agent of the microorganism sample a is fluorescein diacetate), which is projected on the surface of the microorganism sample a. The stage 107 is slidingly moved by the driver unit 108 which is controlled by the microcomputer 106, whereby the microorganism sample a has its whole area scanned automatically. When the microorganisms a' in the microorganism sample a are irradiated with the light, fluorescence is radiated herefrom (refer to FIG. 2). The fluorescence is passed through the objective 112 and is passed via the dichroic mirror 111 through the filter 113 for selecting the specified wavelength of the fluorescence (for example, 530 nm if the staining agent of the microorganism a is fluorescein diacetate) so as to be condensed on the slit 114. Further, the condensed fluorescence is passed through the filter 113' similar to the filter 113, thereby to become reflected light having the specified wavelength.

The reflected light is sensed and converted into an electric signal by the detector 104 of the detection section 103. When passing through the filter unit 105, the electric signal undergoes the limitation of the band of frequencies so as to attenuate currents of frequencies attributed to noise, whereby the noise of the electric signal is reduced. Regarding such electric signals subjected to the frequency band limitation, it is desirable that the detection intensity (slice level) of the signals is appropriately set by observing a waveform on the oscilloscope 115, whereupon only the signals of or above the predetermined intensity are read by the succeeding microcomputer 106.

The electric signal is input to and A/D-converted by the A/D conversion board 116 of the microcomputer 106, and the maximum amplitude value of the resulting data is searched out and read as a fluorescent output value by the microcomputer 106. When the fluorescence from the microorganism sample a has been detected and measured in this way, the movement position of the stage 107, in other words, a scanned position in the microorganism sample a at this time is loaded in the microcomputer 106 by the driver unit 108, and the signal detection position in the microorganism sample a is stored in the microcomputer 106.

Figure 4:
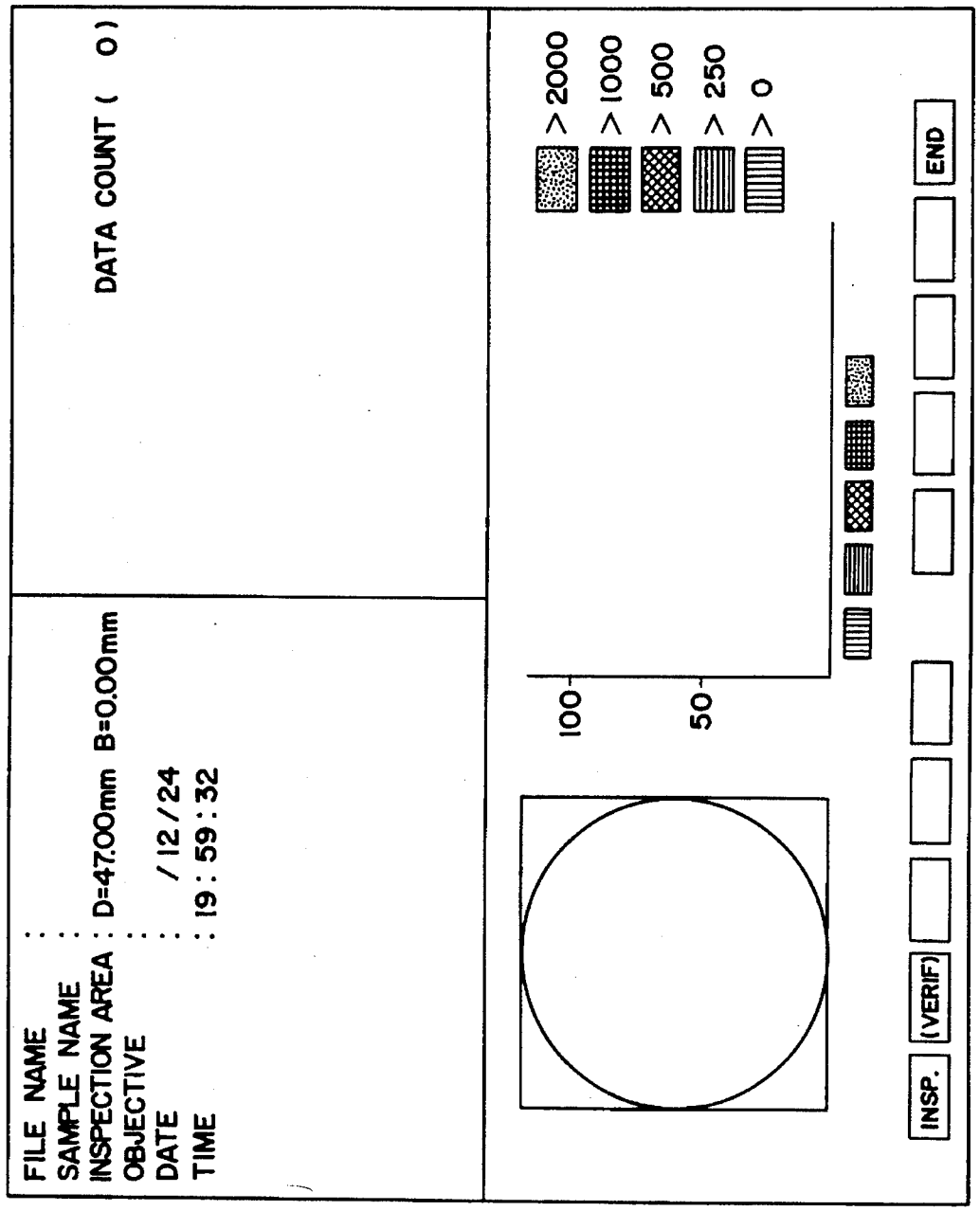
FIG. 4 is an explanatory diagram showing an example of the display of the test results of microorganisms in the detecting apparatus in the first aspect.

The basic operations as stated above are continuously performed over the whole area of the microorganism sample a. Measurement data items with the electric signals read by the microcomputer 106 are processed in this microcomputer 106, whereby the total detection number of the signals of fluorescent substances, the map of the signal detection positions, the histogram of signal detection numbers versus individual fluorescence intensities, etc. are indicated on a display 117 as illustrated in FIG. 4.

After the measurement data items have been output, the function of the microcomputer 106 for verifying the signal detection positions is actuated, whereby the stage 107 stops at the respective detection positions. Here, the operator of the measuring apparatus verifies the microscopic images of the fluorescent substances with the ocular 118 of the fluorescence microscope section 101 so as to discriminate the microorganisms from the other fluorescent substances of the object to-be-inspected, such as auto-fluorescent substances. The unnecessary data of the other fluorescent substances can be deleted on the microcomputer 106.

The measurement data items can be filed and stored in the microcomputer 106, and the file can be drawn out and referred to under the management of the microcomputer 106 at will as may be needed.

Detecting Method and Detecting Apparatus in Second Aspect

A fluorescent-stained microorganism sample for use in a detecting method and a detecting apparatus according to the second aspect of the present invention may well be the same as the microorganism sample for use in the detecting apparatus in the first aspect described before.

Detecting Method

The microorganism detecting method according to the second aspect of the present invention has its basic principle in a method of detecting microorganisms wherein the microorganisms contained in a microorganism sample subjected to fluorescent staining are sensed by microphotometry; characterized by comprising the step of measuring fluorescences emitted by projecting excitation light of at least one wavelength on the microorganism sample, and the step of discriminating the fluorescent-stained microorganisms and any auto-fluorescent foreign matter by utilizing a discrepancy in obtained values selected from the group consisting of spectra, intensities, intensity differences, intensity ratios, and intensity ratio differences of the fluorescences.

Suitable as the excitation lights in the detecting method of the present invention are light of about 545 nm in wavelength (hereinbelow, also called "G excitation light"), one of about 490 nm (hereinbelow, also called "B excitation light"), one of about 405 nm (hereinbelow, also called "V excitation light"), and one of about 365 nm (hereinbelow, also called "U excitation light").

In a case where the microorganism sample is stained with fluorescein (for example, fluorescein diacetate), it is more preferable to employ the B excitation light when one kind of excitation light is used and to employ the B excitation light combined with other excitation light when a plurality of kinds of excitation light are used.

Any desired combination is possible as the combination of excitation lights in the case of employing the excitation lights of a plurality of wavelengths. By way of example, in case of employing the excitation lights of two wavelengths, the four kinds of excitation light B, G, U and V mentioned above can afford combinations B-G, B-U, B-V, G-U, G-V and U-V (no special order of distinction), among which the combinations including B (excitation light), namely, the combinations B-G, B-U and B-V are preferable as stated earlier. Besides, in case of employing the excitation lights of three wavelengths, combinations including B (excitation light), such as combinations B-G-V and B-U-V (no special order of distinction), are mentioned as preferable examples.

In the detecting method of the present invention, the value selected from the group consisting of the spectrum, intensity, intensity difference, intensity ratio and intensity ratio difference of the fluorescence signifies any one among these values or any suitable combination of two or more among them.

In the detecting method of the present invention, a detecting method in which the fluorescent-stained microorganisms and any auto-fluorescent foreign matter are discriminated by utilizing the discrepancy in the fluorescence spectrum consists in obtaining the fluorescence spectrum on the basis of the projection of one excitation light. In case of using the excitation light of one wavelength, one fluorescence spectrum can be obtained, and in case of using the excitation lights of two or more wavelengths in succession, one fluorescence spectrum or a desired number of fluorescence spectra can be obtained.

Here, the fluorescence spectrum signifies the intensities of the fluorescence emitted by the projection of the excitation light as expressed at two or more wavelengths. It shall cover fluorescence intensities expressed at two or more specified wavelengths, and fluorescence intensities continuously expressed in a wavelength region of certain range. Besides, in the case of utilizing the discrepancy in the fluorescence spectrum, there are actually utilized the discrepancy in the values selected from the group consisting of the intensities themselves and intensity differences of fluorescences at two or more wavelengths, and the intensity ratios and intensity ratio differences of fluorescences at two suitable wavelengths.

Here, the intensity signifies each individual intensity value (any of, for example, a, b, . . .) which is obtained by projecting the excitation light of one wavelength or the excitation lights of at least two wavelengths. The intensity difference signifies the difference between the intensity values (as to the above exemplified values, a difference based on any desired combination of, for example, a-b). The intensity ratio signifies the ratio between the intensity values (a ratio based on any desired combination of, for example, b/a) or a ratio containing the intensity difference (a ratio based on any desired combination of, for example, $$\frac{a-b}{a} \text{ or } \frac{c-d}{a-b} ).$$

Lastly, the intensity ratio difference signifies the difference between the intensity ratios (a difference based on any desired combination of, for example, $$\frac{b}{a} - \frac{d}{c}, \text{ or } \frac{a-b}{a} - \frac{c-d}{c} ).$$

In the detecting method of the present invention, one preferable aspect of performance of the detecting method utilizing the discrepancy in the fluorescence spectrum is such that B excitation light having a wavelength of about 490 nm is employed as the excitation light, and that the emitted fluorescences are respectively measured by individually passing them through two sorts of interference filters whose pass bands are centered at wavelengths of 500–600 nm, preferably 510–550 nm, and at wavelengths of 550–700 nm, preferably 560–600 nm, thereby to find the values selected from the group consisting of the intensities, intensity differences, intensity ratios, and intensity ratio differences of the respective fluorescences (Detecting method A).

This detecting method is grounded on the result that, as illustrated in FIGS. 9–12, the fluorescent-stained microorganisms (in this case, a beer yeast: Saccharomyces uvarum stained with fluorescein diacetate (FDA)) exhibit the peak of fluorescence intensities in a wavelength region of 500–550 nm in response to the B excitation light of about 490 nm, whereas the foreign matter having auto-fluorescence exhibits the peak of fluorescence intensities in a wavelength region of 550–700 nm.

In the detecting method A, the fluorescent-stained microorganisms and the auto-fluorescent foreign matter can be discriminated by setting respective reference values for the values of at least two fluorescence intensities in each spectrum, and comparing respective intensity values obtained, with the reference values. Alternatively, they can be discriminated in such a way that respective reference Values for values selected from the group consisting of intensity differences, intensity ratios and intensity ratio differences are set on the basis of the values of at least two fluorescence intensities, that the values selected from the group consisting of the intensity differences, intensity ratios and intensity ratio differences are found on the basis of at least two intensity values obtained for each spectrum, and that the found values are compared with the reference values. In this regard, the use of the intensity ratios is more preferable.

As further preferable aspects of performance of the detecting method utilizing the discrepancy in the fluorescence spectrum, there are mentioned the following two examples in the case of employing a plurality of kinds of excitation light:

As the first example, B excitation light having a wavelength of about 490 nm and V excitation light having a wavelength of about 405 nm are employed as the excitation lights of two wavelengths, and the fluorescences emitted in the B excitation are respectively measured by individually passing them through two sorts of interference filters whose pass bands are respectively centered at wavelengths of 500–600 nm and at longer wavelengths of 550–700 nm, whereby the values selected from the group consisting of the intensities, intensity differences, intensity ratios, and intensity ratio differences of both the fluorescences are found so as to utilize the discrepancy in the fluorescence spectra, while the fluorescences emitted in the V excitation are respectively measured by individually passing them through two sorts of interference filters whose pass bands are respectively centered at wavelengths of 480–530 nm and at longer wavelengths of 510–560 nm, whereby the values selected from the group consisting of the intensities, intensity differences, intensity ratios, and intensity ratio differences of both the fluorescences are found so as to utilize the discrepancy in the fluorescence spectra (Detecting method A').

As the second example, B excitation light having a wavelength of about 490 nm and U excitation light having a wavelength of about 365 nm are employed as the excitation lights of two wavelengths, and the fluorescences emitted in the B excitation are respectively measured by individually passing them through two sorts of interference filters whose pass bands are respectively centered at wavelengths of 500–600 nm and at longer wavelengths of 550–700 nm, whereby the values selected from the group consisting of the intensities, intensity differences, intensity ratios, and intensity ratio differences of both the fluorescences are found so as to utilize the discrepancy in the fluorescence spectra, while the fluorescences emitted in the U excitation are respectively measured by individually passing them through two sorts of interference filters whose pass bands are respectively centered at wavelengths of 420–500 nm and at longer wavelengths of 480–580 nm, whereby the values selected from the group consisting of the intensities, intensity differences, intensity ratios, and intensity ratio differences of both the fluorescences are found so as to utilize the discrepancy in the fluorescence spectra (Detecting method A").

In the detecting method A' or A" as defined above, the comparisons in the detecting method A between the reference values and the values selected from the group consisting of the intensity values, intensity differences, intensity ratios and intensity ratio differences are made for each of the excitation lights. Accordingly, such a detecting method can be effectively adopted in a case, for example, where microorganisms and the foreign matter are to be discriminated more definitely or where they are difficult of discrimination with only one kind of excitation light.

In the detecting method of the present invention, one preferable aspect of performance of the detecting method which utilizes the discrepancy in the value selected from the group consisting of the intensity, intensity difference, intensity ratio and intensity ratio difference of fluorescence is such that B excitation light having a wavelength of about 490 nm and G excitation light having a wavelength of about 545 nm are employed as the excitation lights of two wavelengths, and the emitted fluorescences are respectively measured by passing them through interference filters whose pass bands are respectively centered at wavelengths of 500–600 nm, preferably 510–550 nm, and at longer wavelengths of 550–700 nm, preferably 560–600 nm, thereby to find the values selected from the group consisting of the intensities, intensity differences, intensity ratios, and intensity ratio differences of both the fluorescences (Detecting method B) (here, the intensities, intensity differences, intensity ratios and intensity ratio differences signify the contents as defined earlier).

This detecting method is grounded on the discrepancy in the intensities of both the fluorescences which are emitted by projecting the B excitation light of about 490 nm and the G excitation light of about 545 nm, as illustrated in FIGS. 9–12. In the detecting method B, the fluorescent-stained microorganisms and the auto-fluorescent foreign matter can be discriminated in such a way that, as to the two fluorescence intensities obtained, the values selected from the group consisting of the intensity values, intensity differences, intensity ratios and intensity ratio differences of the fluorescences are compared with the respective reference values similarly to the detecting method A. In this regard, the use of the first-mentioned intensity values is more preferable.

In the detecting method of the present invention, the fluorescent-stained microorganisms and the auto-fluorescent foreign matter can be more reliably discriminated by utilizing both the discrepancy in the spectra of fluorescences and the discrepancy in the values selected from the group consisting of the intensities, intensity differences, intensity ratios and intensity ratio differences of the fluorescences. One preferable aspect of performance of such a detecting method consists in that, after the fluorometry in the detecting method A, the fluorometry in the detecting method B is carried out to find the fluorescence spectra and the values selected from the group consisting of the intensities, intensity differences, intensity ratios, and intensity ratio differences of the fluorescences (Detecting method C).

In this detecting method, the fluorescent-stained microorganisms and the auto-fluorescent foreign matter can be discriminated by setting respective reference values for the spectra of the fluorescences and for the values selected from the group consisting of the intensities, intensity differences, intensity ratios and intensity ratio differences of the fluorescences, and then comparing corresponding values obtained, with the reference values.

By the way, as the detecting method which utilizes both the discrepancy in the spectra of the fluorescences and the discrepancy in the values selected from the group consisting of the intensities, intensity differences, intensity ratios and intensity ratio differences of the fluorescences, it is also possible to adopt a method in which the fluorometry in the detecting method B is carried out before the fluorometry in the detecting method C.

Detecting Apparatus

The microorganism detecting apparatus according to the second aspect of the present invention has its basic principle in the detecting method as described above, and it consists in an apparatus for detecting microorganisms having microphotometric means for sensing the microorganisms contained in a microorganism sample subjected to fluorescent staining; characterized by comprising light-source projection means for projecting excitation light of at least one wavelength on the microorganism sample, detection means for detecting and photoelectrically converting fluorescences emitted from the microorganism sample, and signal processing means for reading output values of signals from said detection means so as to find values selected from the group consisting of spectra, intensities, intensity differences, intensity ratios, and intensity ratio differences of the fluorescences, and for measuring the fluorescent-stained microorganisms in discrimination from any auto-fluorescent foreign matter on the basis of a discrepancy in the found values.

Now, the detecting apparatus in the second aspect of the present invention will be described in more detail in conjunction with preferred practicable examples shown in FIGS. 5–7.

Figure 5:
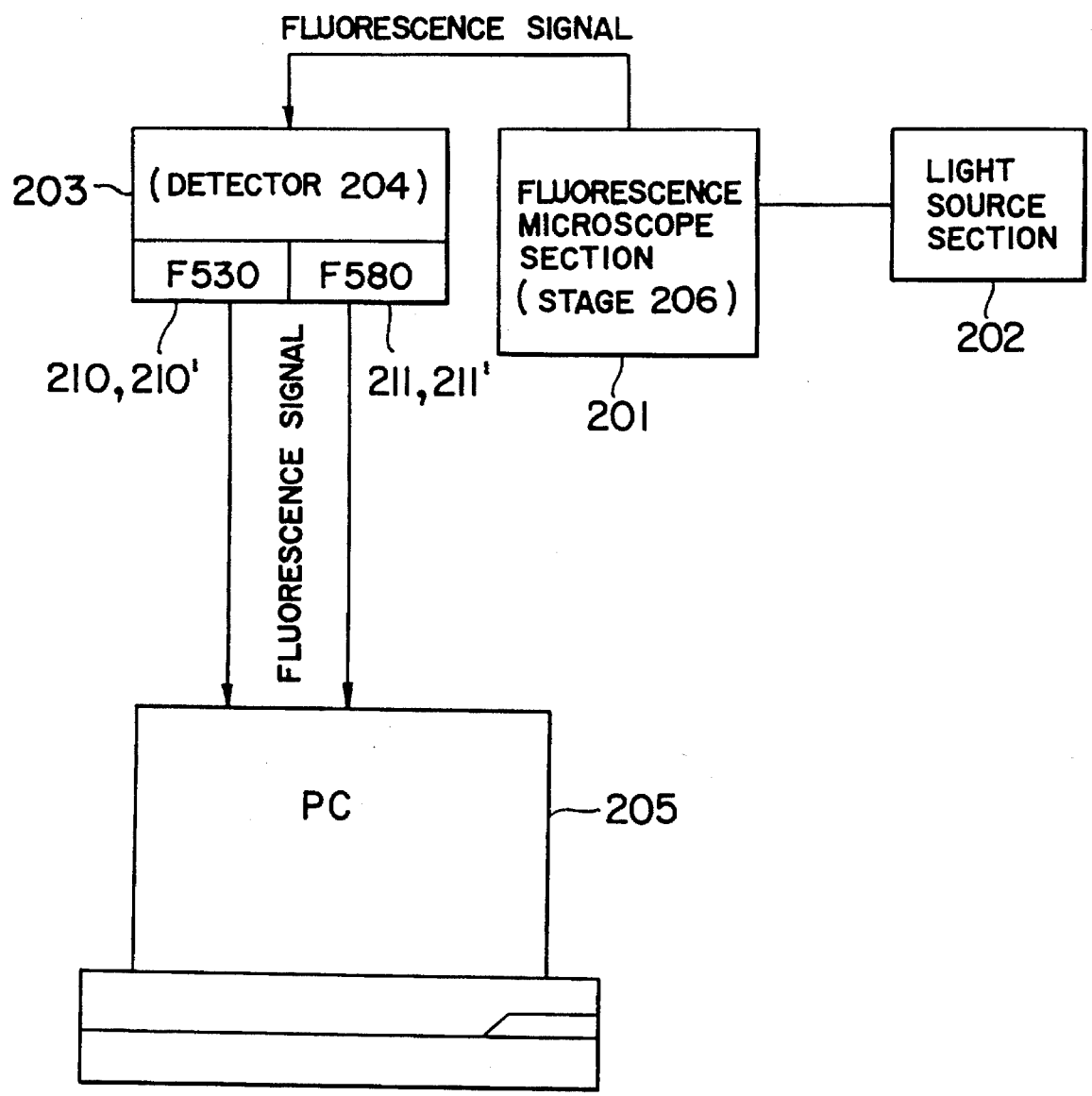
FIG. 5 is an explanatory block diagram showing an example of the fundamental construction of a detecting apparatus according to the second aspect of the present invention.

The detecting apparatus in the preferred form according to the present invention is fundamentally illustrated in FIG. 5, and it comprises a fluorescence microscope section 201 which is furnished with a motor-driven stage 206 for placing therein a microorganism sample a subjected to fluorescent staining, and light source means (including a light source unit 202) for projecting excitation light of predetermined wavelength on the sample a; a detection section 203 which detects and photoelectrically converts fluorescence from the microorganism sample a; and a microcomputer (PC) 205 which serves as signal processing means for reading and arithmetically processing the output value of a signal from the detection section 203.

Figure 6:
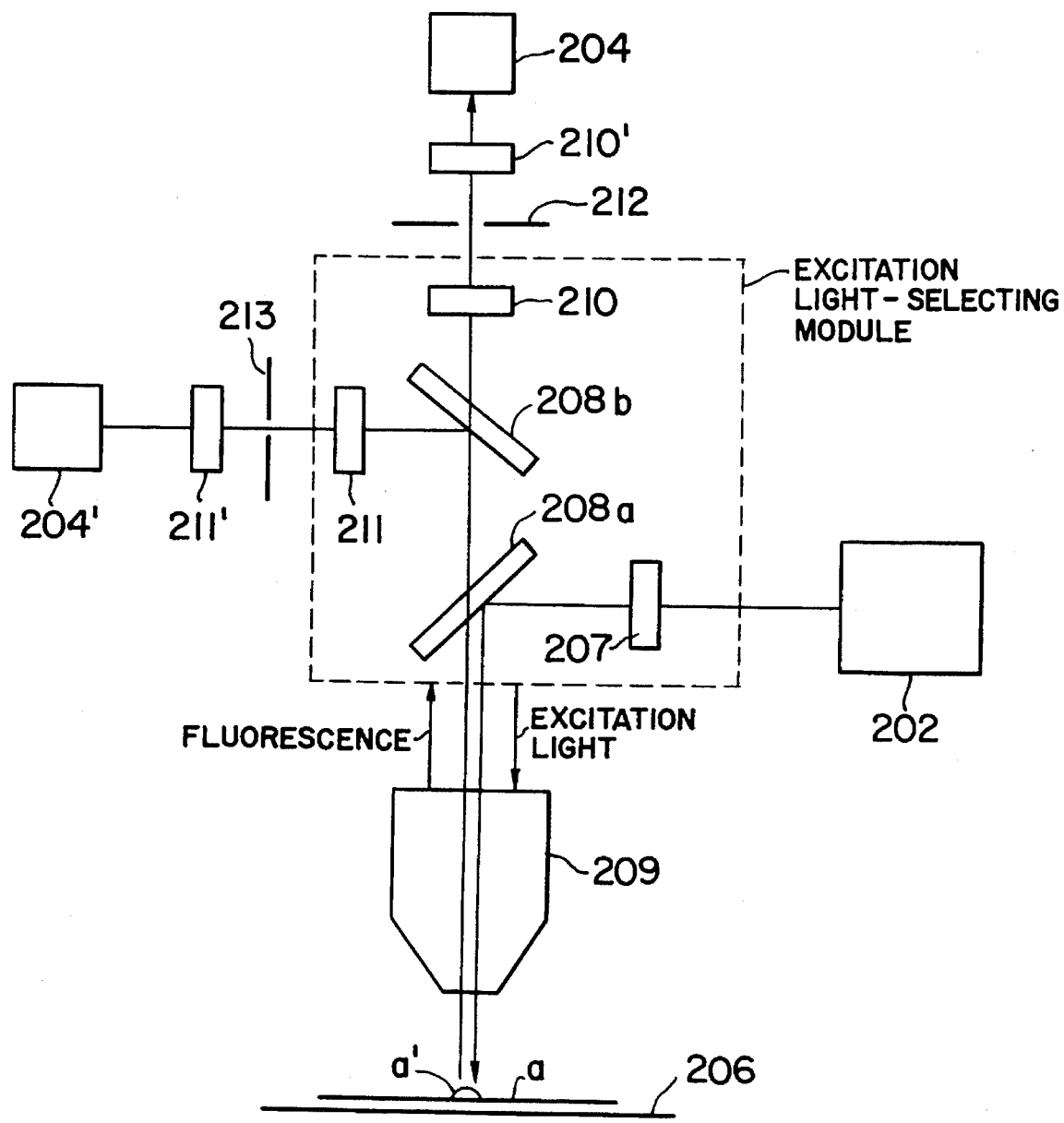
FIG. 6 is an explanatory diagram showing an example of the fundamental construction of a microfluorometer section included in the apparatus in FIG. 5.

The fluorescence microscope section 201, the light source section 202 and the detection section 203 construct a microfluorometer section, the major practicable constituents of which are shown in FIG. 6.

The microfluorometer section comprises the light source section 202 such as a mercury-arc lamp or xenon-arc lamp; the motor-driven stage 206 on which the microorganism sample a is placed; a filter 207 for selecting the excitation light, a dichroic mirror 208a and an objective 209 which are disposed in an optical path extending from the light source section 202 to the stage 206; a dichroic mirror 208b which splits into two optical paths the fluorescence emitted from the sample a by the projection of the excitation light from the light source section 202; first filters 210, 210' and second filters 211, 211' which serve to select the specified wavelengths of the branched fluorescences passing through the respective optical paths; slits for diaphragms 212 and 213 which are interposed between the filters in the respective paths; and detectors 204 and 204' such as photomultiplier tubes, photodiodes or phototransistors, which detect and photoelectrically convert the fluorescences of the microorganism sample a having passed through the slits as well as the filters and which are preferably the photomultiplier tubes.

The excitation light selecting filter 207 is for B excitation at a wavelength of about 490 nm, or (and) for G excitation at a wavelength of about 545 nm. The first filters 210 and 210' are interference filters which pass a wavelength region centered at 500–600 nm, preferably 510–550 nm, and which correspond to the case where the filter 207 is for the B excitation. On the other hand, the second filters 211 and 211' are interference filters which pass a wavelength region centered at 550–700 nm, preferably 560–650 nm, and which correspond to the case where the filter 207 is for the G excitation.

Moreover, in the present invention, the excitation light V or U can be used as in the detecting method described earlier. It is needless to say that, in this case, a filter for V excitation at a wavelength of about 405 nm or for U excitation at a wavelength of about 365 nm can be employed as the excitation light selecting filter 207. On this occasion, the detecting apparatus can be so constructed that, as described in the detecting method, regarding the V excitation light, interference filters which pass wavelength regions centered at 480–530 nm and at 510–560 nm are respectively applied to the first filters 210, 210' and the second filters 211, 211', while regarding the U excitation light, interference filters which pass wavelength regions centered at 480–580 nm and at 420–500 nm are respectively applied to the first filters 210, 210' and the second filters 211, 211'.

Figure 8:
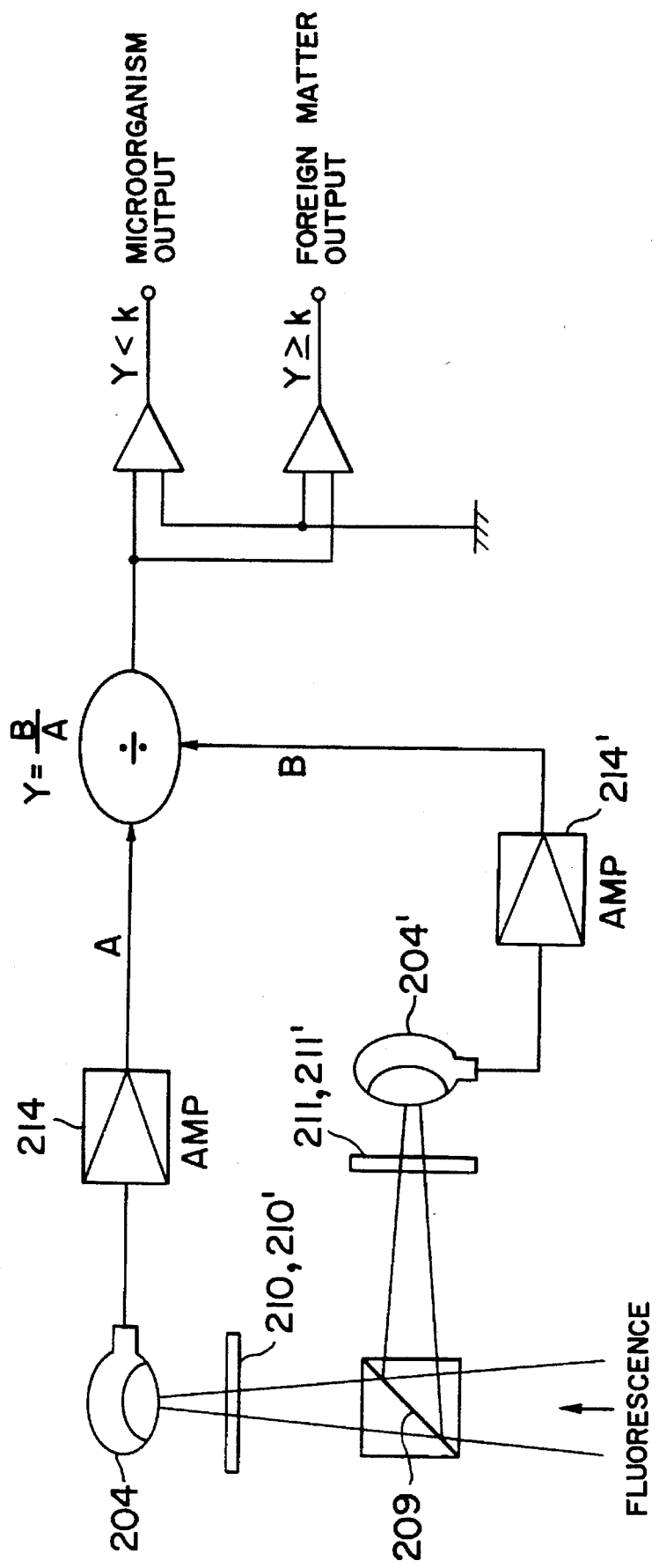
FIG. 8 is an explanatory diagram showing a signal circuit for discriminating microorganisms in the detecting apparatus in the second aspect of the present invention.
Figure 9:
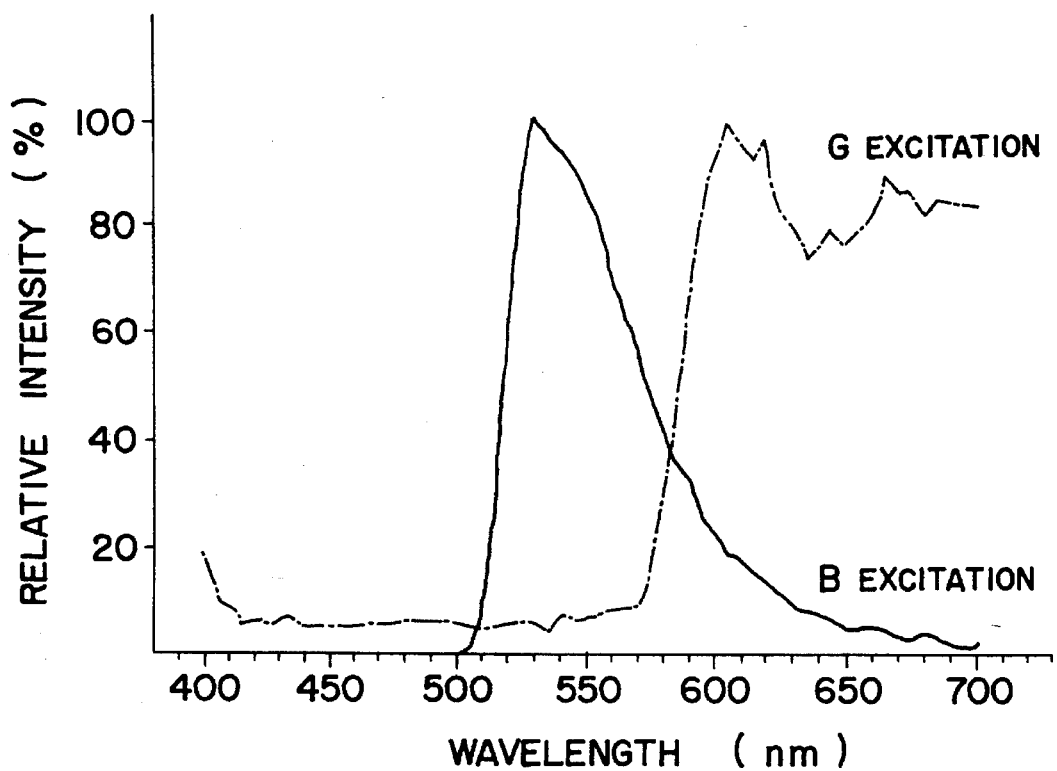
FIG. 9 shows the fluorescence spectrum of a beer yeast subjected to fluorescent staining.
Figure 10:
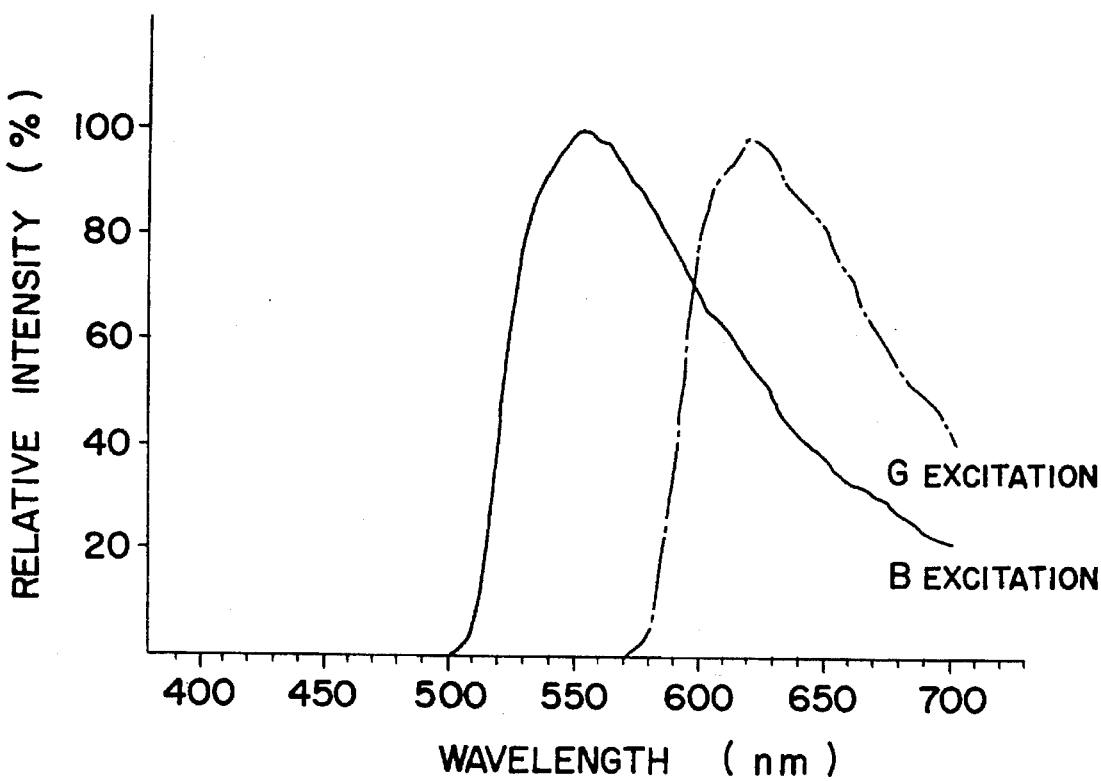
FIG. 10 shows the fluorescence spectrum of an auto-fluorescent foreign matter contained in black tea.

Although the two detectors are provided in FIGS. 6–8, it is also possible to split the fluorescence emitted from the sample a, into three or more optical paths and to provide three or more necessary arrangements including the detectors, in correspondence with the optical paths.

The signal processing means, for example, microcomputer 205 subjects the electric signals from the detection section 203 to A/D (analog-to-digital) conversion and reads the output values of the signals, finds values selected from the group consisting of the spectra, intensities, intensity differences, intensity ratios and intensity ratio differences of the fluorescences as described earlier in the detecting method of the present invention, and compares the found values with the respective reference values stored beforehand, thereby functioning to measure the fluorescent-stained microorganisms in discrimination from the auto-fluorescent foreign matter.

The detecting apparatus of the present invention constructed as stated above has featuring functions to be listed below:

(1) Fluorescence Analyzing Functions:
<1> Fluorescence spectrum analyzing function;

As illustrated in FIGS. 6–8, in the case of employing the B excitation light, the fluorescences emitted in response to the B excitation light (having the wavelength of about 490 nm) and passed through the filters of the two unequal wavelength regions, namely, the interference filter whose pass band is centered at the wavelengths of 500–600 nm and the interference filter whose pass band is centered at the wavelengths of 550–700 nm are respectively received and converted into the electric signals by the two detectors 204 and 204', whereby the discrepancy between the fluorescence spectrum of the fluorescent-stained microorganisms and that of the auto-fluorescent foreign matter can be automatically analyzed at high efficiency.

<2> Function of detecting fluorescence intensities responsive to different excitation lights;

The data items of fluorescence intensities are obtained using the interference filter centered at the wavelengths of 500–600 nm, for the B excitation light, and the interference filter centered at the wavelengths of 550–700 nm, for the G excitation light.

<3> Functions of analyzing fluorescence spectrum and detecting fluorescence intensities;

The fluorescence spectrum responsive to the excitation light of one wavelength region and the fluorescence intensities responsive to the two excitation lights of unequal wavelength regions are obtained by combining the functions <1> and <2>.

(2) Fluorescence Analysis Result Processing Functions:
<1> Function of calculating results of fluorescence spectrum analysis;

The received light signals of at least two detectors are calculated to obtain the ratios between the outputs of the detectors, namely, the ratios between the fluorescence intensities, or the intensities of the respective fluorescences, and the obtained values are compared with the reference values, whereby the microorganisms are automatically detected in discrimination from the foreign matter.

<2> Function of processing fluorescence intensity results;

A plurality of fluorescence intensities obtained with a plurality of kinds of excitation light, for example, two fluorescence intensities obtained with two kinds of excitation light are compared with the reference values, or the intensities of the two fluorescences are calculated to find the intensity ratio, which is then compared with the reference value, whereby the microorganisms are automatically detected in discrimination from the foreign matter.

A function based on the combination of the functions (1)-<1> and (2)-<1> corresponds to the detecting method A of the present invention. Signal processing for the discrimination of the microorganisms in this case is executed by a signal processing circuit shown in FIG. 8 by way of example. Referring to the figure, fluorescence emitted from the microorganism sample by the projection of the B excitation light is split into two optical paths by the dichroic mirror 209. One of the resulting fluorescences is passed through the first filters 210, 210' on the shorter wavelength side and is thereafter sensed and photoelectrically converted by the detector 204, and the electric signal thus produced is amplified by an amplifier 214, whereby a fluorescence intensity value A is obtained. The other fluorescence is passed through the second filters 211, 211' on the longer wavelength side and is thereafter sensed and photoelectrically converted by the detector 204', and the electric signal thus produced is amplified by an amplifier 214', whereby a fluorescence intensity value B is obtained. The fluorescence intensity values A and B obtained are arithmetically processed to find the fluorescence intensity ratio (Y). Further, the intensity ratio is compared with the corresponding reference value k. Depending upon, for example, whether or not the Y value is smaller than the reference value k, the microorganisms are detected in discrimination from the foreign matter.

A function based on the combination of the functions (1)-<2> and (2)-<2> corresponds to the detecting method B of the present invention. Signal processing for the discrimination of the microorganisms in this case is executed in such a way that, as to the two fluorescence intensities obtained by projecting the excitation lights of the two, first and second wavelengths (the B excitation light and the G excitation light), signal processing means compares and processes the respective values with two reference values, or that the ratio of the intensities is calculated and is compared with the corresponding reference value similarly to the above.

Besides, a function based on the combination of the functions (1)-<3> and (2)-<1>, <2> corresponds to the detecting method C of the present invention. Signal processing for the discrimination of the microorganisms in this case is executed in such a way that the fluorescence spectra obtained, and the values selected from the group consisting of the intensities and intensity differences of the fluorescences and the intensity ratios and intensity ratio differences calculated from the intensities are compared with the respective reference values by signal processing means. Therefore, the discrimination of the microorganisms becomes more accurate.

A construction which comprises in combination the detecting apparatus according to the second aspect of the present invention and the detecting apparatus according to the first aspect described before, is also covered within the scope of the detecting apparatus in the second aspect of the present invention. More specifically, in the detecting apparatus, as shown in FIG. 7, a signal filter unit 215 is disposed at a stage posterior in terms of the electric signals of the microfluorometer section, that is, at a stage posterior to the detectors 204 204', whereby noise ascribable to the electric signals from the detection unit 203 can be reduced. The filter unit 215 passes only currents of specified frequency band, and it can be formed of a band-limiting circuit arrangement which is generally employed in the fields of communications etc. In addition, an oscilloscope 216 for observing the variation of the waveform of each signal may well be provided. It is desirable that the detection intensity of each signal from the signal filter unit 215 is set by the oscilloscope 216 so as to cut off signals lower than the predetermined intensity, whereby the microcomputer 205 to be described below is caused to read only the specified signal as desired. Further, the detecting apparatus of the present invention can be furnished with a driver unit 217 and an X-Y stage scanner 218 as shown in FIG. 7, for affording a function which permits the whole area of the microorganism sample to be automatically scanned in accordance with the automatic fluorescence inspection program of the microcomputer 205. It is also possible to endow the signal processing function of the microcomputer 205 with the function of displaying inspection data and the function of filing the inspection data.

Thus far, the detecting apparatus in the second aspect of the present invention has been concretely described with reference to the drawings. As understood from the foregoing, the detecting apparatus of the present invention can adopt any of the desired constructions corresponding to the detecting methods of the present invention elucidated earlier, regarding various conditions such as the kinds of excitation lights and the combination thereof, the wavelengths of the interference filters and the combination thereof, and the combination of the values for the comparisons with the reference values, selected from the group consisting of the fluorescence spectra, intensities, intensity differences, intensity ratios and intensity ratio differences.

Examples of microorganism measurements with the measuring apparatuses according to the present invention will now be described, but the present invention shall not be restricted thereto.

Example A1:

Live fungi of a yeast (Saccaromyces uvarum) numbering 84 were mixed in 100 ml. of a black tea drink (a product of Kirin Beer Brewery). The resulting black tea was suction-filtered by a filter (Nuclepore Filter manufactured by Nomura Microscience Inc.) having a diameter of 47 nm and a pore size of 0.4 micron, and the filter was washed with sterile water. Thereafter, the fungi were cultured on malt agar at 25° C. for 15 hours to form a minute colony (number of yeasts: 4–$10^1$ cells). The resulting filter was stained with fluorescein diacetate at a concentration of 100 μmol (pH 5.3) for 15–30 minutes, and was thereafter washed with water from the rear surface thereof for 2 minutes. After the filter was air-dried, it was fixed on a slide glass piece of 57×76 mm² with an acetone solution. Thus, a sample to be tested was prepared.

Using the detecting apparatus according to the first aspect of the present invention, the sample was automatically inspected under the conditions that the photomultiplier tube 104 was operated by a voltage of 500 volts, that the objective 112 had a magnification of 10 diameters, that the slit 114 had an area of 2×1 mm², that the slice level of a signal intensity was set at +0.9—1.0 volt, that a signal filter was adapted to pass a region of 4–250 Hz, that the projected excitation light had a wavelength of 490 nm (B excitation), and that the interference filters 113, 113' of the reflected light receiving portion had a pass band centered at 530 nm. As a result, fluorescences were detected at 104 positions. In addition, 84 colonies were microscopically verified (detection rate:

100%). The remaining 20 fluorescent positions were of microscopic auto-fluorescent substances peculiar to the product.

Example A2:

296 fungi of a yeast (Saccharomyces uvarum) were mixed in 633 ml. of bottled beer (corresponding to one large bottle), and the beer was treated similarly to Example A1, to prepare a sample to-be-tested. However, the culture was conducted at 25° C. for 12 hours. Using the detecting apparatus in the first aspect of the present invention, the sample was automatically inspected under the same conditions as in Example A1 except a photomultiplier tube voltage of 519 volts. As a result, fluorescences were detected at 445 positions. As the result of microscopic verification, 260 colonies were verified (detection rate: 88%).

A cause for an overlooking or missing rate of about 12% was conjectured to be the adjacency of auto-fluorescent substances.

Example A3:

47 yeast cells were mixed in 100 ml. of a physiological saline solution, and a sample having the fluorescent-stained yeast was prepared in conformity with Example A1. In the example here, quite no culture was conducted (accordingly, the yeast of unit cells, not colonies, was put into use). Using the detecting apparatus in the first aspect of the present invention, the sample was automatically inspected under the same conditions as in Example A1 except an objective magnification of 20 diameters and a slit area of 4×2 mm$^2$. As a result, fluorescences were detected at 83 positions. As the result of microscopic verification, 47 yeast cells were verified (detection rate: 100%).

Example B4:

A yeast (S. uvarum) was mixed in a drink on the market (a product of Kirin Beer Brewery), each of auto-fluorescent substances contained in the drink was caught on a filter (Nuclepore Filter manufactured by Nomura Microscience Inc.) having a pore size of 0.4 micron together with the yeast, and the yeast and the auto-fluorescent substance were stained with fluorescein diacetate (FDA). The resulting filter was sufficiently washed with water. As to samples thus obtained, fluorescence spectra were measured by employing the exciting filter of 490 nm for the B excitation (as shown at numeral 207 in FIG. 6) and by setting the shorter wavelength and longer wavelength of the absorbing filters (210, 210' and 211, 211') at 530 nm and 580 nm, respectively, in the signal processing circuit in FIG. 8 for discriminating the fluorescent-stained microorganisms and the auto-fluorescent foreign matters. The signal processing results of the fluorescent-stained yeast and the auto-fluorescent foreign matters contained in the drink were as listed in Table 1. In view of these results, the microorganisms and the foreign matters can be readily discriminated by setting the value k in FIG. 8 to, for example, 0.7.

TABLE 1

Signal Processing Results of Spectrum of Foreign Matters in Drink on Market

|  | Micro- (*1) organisms | Auto-fluorescent Foreign Matters (*2) | | | | | | | | |
|---|---|---|---|---|---|---|---|---|---|---|
|  |  | A | B | C | D | E | F | G | H | I |
| Fluorescence intensity ratio (Y = 580 nm/530 nm) | 0.42 | 1.10 | 0.84 | 1.20 | 1.45 | 0.92 | 1.11 | 0.75 | 1.02 | 0.79 |

(*1) Yeast stained with FDA
(*2) Auto-fluorescent foreign matters contained in Drink on Market
A Straight black tea, Yellow
B Straight black tea, Green
C Ptisan, Yellow
D Ptisan, Brown
E Oolong tea, Fibrous, Yellow
F Oolong tea, Yellow
G Foreign Matter 1 in Draught beer on market
H Foreign Matter 2 in Draught beer on market
H Foreign Matter 3 in Draught beer on market Example B5:

The same samples as in Example B4 were scanned by the two wavelengths of 490 nm (B excitation) and 545 nm (G excitation) at which the exciting filters were set, and fluorescence intensities were measured using the absorbing filters of 530 nm and 620 nm, respectively. Then, results listed in Table 2 were obtained. In view of the results, only the microorganisms can be detected by setting the respective constants so as to hold (fluorescence value at the B excitation)>$a_1$ and (fluorescence value at the G excitation)<$a_2$. It is understood from Table 2 that the microorganisms can be discriminated 100% when $a_1$=400 (Au) and $a_2$=200 (Au) are set by way of example.

TABLE 2

Fluorescence Intensities (in Au) of Foreign Matters in Drink on Market responsive to B Excitation and G Excitation

|  | (Note) Micro-organisms | Auto-fluorescent Foreign Matters | | | | | |
|---|---|---|---|---|---|---|---|
|  |  | A | B | C | D | E | F |
| B excitation | 589 | 2895 | 1429 | 1091 | 900 | 339 | 1791 |
| G excitation | 88 | 2939 | 551 | 768 | 1176 | 200 | 1141 |

(Note) Samples in the Table are the same as in Table 1.

Example B6:

A yeast (S. uvarum) was added in drought beer on the market (a product of Kirin Beer Brewery), each of auto-fluorescent foreign matters contained in the drought beer was caught on the filter having the pore size of 0.4 micron (Nuclepore Filter) together with the yeast, and the yeast and the foreign matter was stained with FDA in the same manner as in Example B4. As to samples thus obtained, fluorescence intensity ratios were measured by employing the exciting filter of 490 nm for the B excitation (as shown at numeral 207 in FIG. 6) and by setting the shorter wavelength and longer wavelength of the absorbing filters (210, 210' and 211, 211') at 530 nm and 580 nm, respectively, in the signal processing circuit in FIG. 8 for discriminating the fluorescent-stained microorganisms and the auto-fluorescent foreign matters. As a result, as listed in Table 3, five among the seven auto-fluorescent foreign matters could be discriminated from the fluorescent-stained microorganisms by setting the value k in FIG. 8 to, for example, 0.7. Further, it has been revealed that the remaining two auto-fluorescent foreign matters (auto-fluorescent foreign matters 1 and 3), which could not be discriminated from the fluorescent-stained microorganisms in the B excitation method here, can be discriminated from the fluorescent-stained yeast by measuring fluorescence intensity ratios by the use of the exciting filter of 405 nm (for the V excitation) and with the shorter wavelength and longer wavelength of the absorbing filters set at 500 nm and 520 nm, respectively, and by setting the value k in FIG. 8 to, for example, 1.0.

TABLE 3

Method of Discriminating Fluorescent-stained Yeast from Auto-fluorescent Foreign Matters in Draught Beer as based on Fluorescence Intensity Ratios

| | Fluo-rescent-stained Yeast | Auto-fluorescent Foreign Matters | | | | | | |
|---|---|---|---|---|---|---|---|---|
| | | 1 | 2 | 3 | 4 | 5 | 6 | 7 |
| B excitation 580 nm/ 530 nm | 0.43 | 0.36 | 0.75 | 0.48 | 0.72 | 1.02 | 0.76 | 0.79 |
| V excitation(*) 520 nm/ 500 nm | 0.79 | 1.16 | — | 1.15 | — | — | — | — |

(*)The V excitation method was performed for the fluorescent-stained yeast and the auto-fluorescent foreign matters 1 and 3.

As previously explained, an important feature of one aspect of the invention is that means are provided for limiting a band of frequencies ascribable to noise in relation to the signal provided by fluorescence from a microorganism. This is now further described.

As shown in FIG. 3, a signal filter unit 105 is used for passing only a specified frequency band. As previously explained, suitable filters for passing selected frequencies within a pass band are known, hence not described herein.

The selection of the desired pass band, for passing information relevant to the fluorescence from the samples, while rejecting frequencies caused by electrical noise, is described in connection with FIG. 13.

Figure 13:
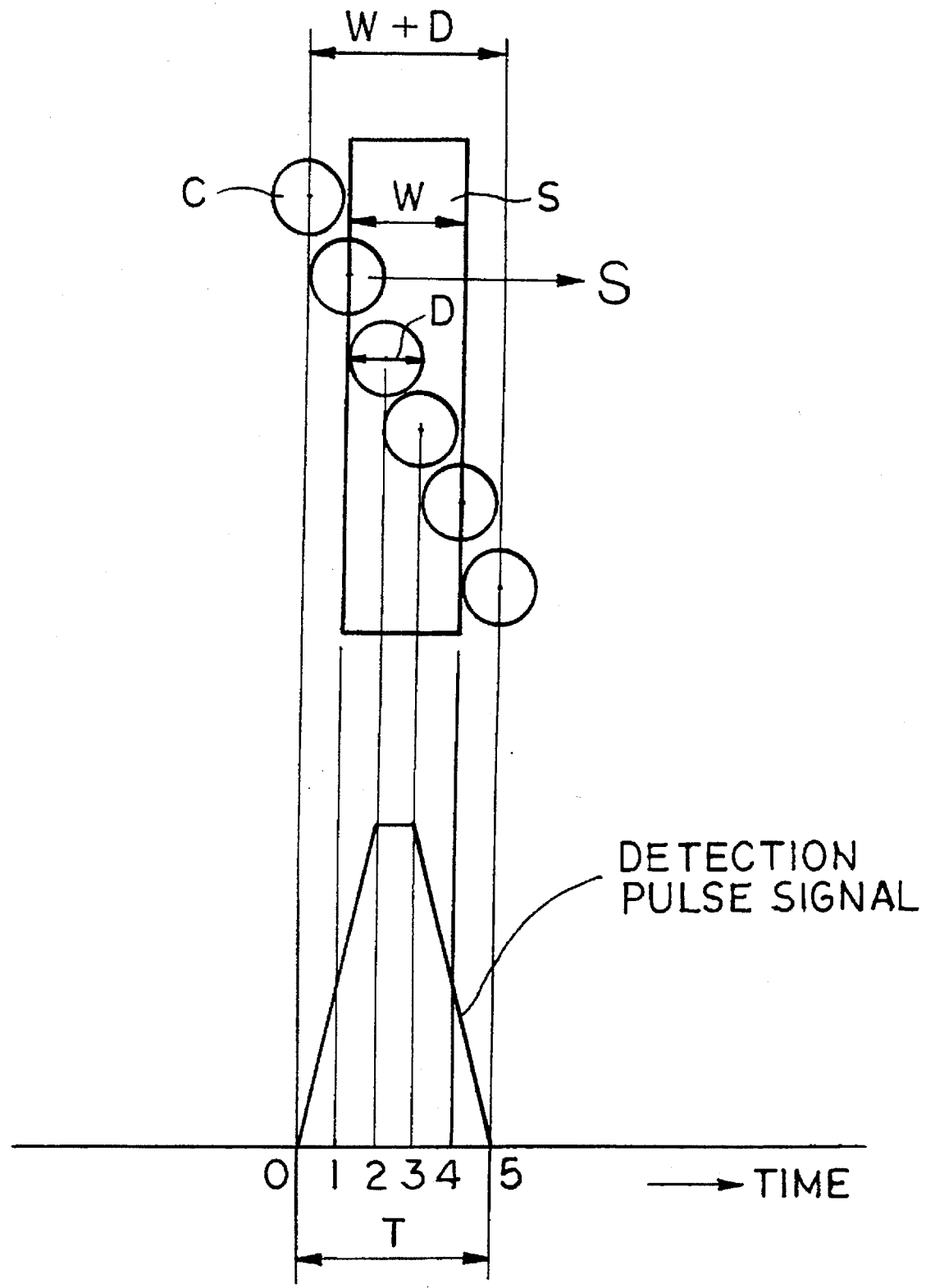
FIG. 13 is a drawing illustrating the scanning of a single microorganism colony on a glass side.

FIG. 13 shows, in its upper half, an illustration of an image of the slit 114 (FIG. 2) on the sample being scanned. With respect to the sample, the width of the area of the sample which is viewable through the slit 114 at any moment is equal to the actual width of the slit 114 divided by the magnification of the object lens 112. During the scanning of the sample, the image of the slit moves across the surface of the sample and successive areas on the sample surface pass within the field of view of the slit.

As indicated by the arrow S, the sample is being moved with respect to the slit from left to right. The viewing of a single colony C of microorganisms is shown with the exposure of the colony C through the slit at successive intervals of time being illustrated by the vertically spaced apart circles C. Thus, at T=0, the colony C is not within the slit; at T=1, one half of the diameter D of the colony is viewable through the slit; at T=2, the whole diameter D of the colony first becomes visible; and finally, at T=5, the colony C is no longer visible through the slit.

The curve in the lower half of FIG. 13 shows the detected light signal obtained from viewing the colony C through the slit. The amplitude of the signal is a direct function of the area of the colony C being viewed because the entire surface of the colony is emitting light. Useful information provided by the fluorescence from the colony is thus provided during the time T, referred to as the width of the detection pulse signal.

Such width, T, corresponds to the period from the time when the center of the colony C is at a distance of D/2 to the left side of the slit image to the time when it reaches a distance D/2 to the right side of the slit image. Accordingly, the pulse signal width T is represented by $T=(W+D)/S$ [sec], where T is the width (duration) of the detection pulse signal, W is the width of the image of the slit on the sample, i.e., the actual slit width divided by the magnification of the object lens, D is the diameter of the colony, and S is the scanning velocity of the sample surface.

For a signal having a pulse duration or period T, the pulse rate R of the signal corresponding to the scanning of colonies of diameter D is:

$R=1/T=S/(W+D)$ [Hz].

Thus, in the case of detecting colonies in the range between D=1 μm and D=100 μm, the frequency range from the pulse rate $R_1$ for D=1 μm to the pulse rate $R_2$ or D=100 μm is the basic pass band of the signal filter.

Examples are as follows:

(A) In the case where S=10 [mm/sec] and W=0.2 [mm],
 a) With respect to D=1 [μm], R=10/(0.2+0.001)~50 [Hz]
 b) With respect to D=100 [μm], R=10/(0.2+0.1)~35 [Hz]
 c) Accordingly, the basic pass band is between 50 [Hz] and 35 [Hz].

(B) In the case where S=12 [m/sec] and W=0.1 [mm],
 a) With respect to D=1 [μm], R=12/(0.2+0.0001)~60 [Hz]
 b) With respect to D=100 [μm], R=12/(0.2+0.1)~40 [Hz]
 c) Accordingly, the basic pass band is between 60 [Hz] and 40 [Hz].

(C) In the case where S=10 [m/see] and W=0.1 [mm], likewise, the basic pass band comes to between 100 [Hz] and 50 [Hz].

(D) In the case where S=12 [mm/sec] and W=0.1 [mm], the basic pass band comes to between 120 [Hz] and 60 [Hz].

Thus, with colonies on a given sample slide having a determined range of diameters, the upper and lower cut-off frequencies of the filter pass band are selected to pass pulse frequencies corresponding to the smallest and largest colonies on the sample slide. As a practical matter, because the gain characteristics of typical electrical filters are not flat in the vicinity of the cut-off frequencies, it is preferable to select, as the upper frequency of the pass band, a frequency two or three times the maximum calculated pulse rate.

As known in the photographic imaging art, a diaphragm is used to attain two objects, namely to control a focal depth and to limit a visual field. The former is call as an aperture stop and the latter is call an a field stop.

The slit of the present invention is used for a different object, namely to define the range of modulation frequency of the fluorescent light to be sensed from a sample. This modulation frequency has a value in relation to the size of a microorganism to be detected, said value being generally in the range of 10 Hz order to 100 Hz order. Please note that the modulation frequency is different from the frequency of fluorescent light itself (on the order of $10^{14}$ Hz).

Further, the signal filter 105 is different from the optical filter. Namely, the optical filters (113, 133', 210, 210', 211, 211') are used to selectively extract the specific fluorescent light of the specific color which is coming from the sample.

The fluorescent light coming from a microorganism, which is passed through the optical filter, has modulation frequencies within the frequency band (generally in the range of 10 Hz order to 100 Hz order) which is limited by the width of the slit, the scanning speed and the size of microorganism. This fluorescent light is inputted to a photocell in which the light is converted into an electric signal, and then this electric signal is inputted to the signal filter 105 through which only the signal component having the modulation frequencies within the aforesaid limited frequency band are extracted and the other signal components are eliminated as noise. Thereby the electric signal components indicating the presence of a microorganism can be extracted with high precision.

As mentioned above, the optical filter is used for the purpose to limit the color range of the fluorescent light to be sensed within that of the fluorescent light coming from a sample. In the disclosed embodiments, optical filters are provided in a section 101 in FIG. 1 and they are, for example, filters 113, 113' in FIG. 2 and filters 210, 210', 211,211' in FIG. 6. On the other hand, the signal filter means is used for the purpose to limit the modulation frequency band of electric signal components to be processed to the frequency band indicating the presence of a microorganism.

The frequency band indicating the presence of the microorganisms is defined by the width the slit, the sample scanning speed and the size of microorganisms (or their colonies).

One of the characteristic features of the present invention exists in that by taking out only the signal components indicating the presence of a microorganism, i.e. having modulation frequencies within the limited frequency band which is defined by the width of the slit, the sample scanning speed and the size of the microorganisms, from among various modulation frequency components of the electric signals outputted from the photocell, it is possible to obtain a high S/N ratio of the electric signals to be processed for microorganism detection.

Another characteristic feature is that two light frequency bands are used between which there is a more remarkable difference of the light intensity in the fluorescent spectrum coming from the microorganism than in the fluorescent spectrum coming from the foreign matter.

Another characteristic feature is that two excitation lights are used in which one excitation light causes no distinct difference in the intensity between the fluorescent light from the foreign matter, and the other excitation causes a distinct difference.

What is claimed is:

1. An apparatus for detecting fluorescent substances in a microorganism sample, the apparatus comprising:

stage means for placing thereon a microorganism sample subjected to fluorescent staining, and for transporting the sample to permit the same to be scanned;

light source means for protecting excitation light of a predetermined wavelength onto the sample so that a fluorescent light is originated from the sample;

slit means having a slit of a predetermined width through which the fluorescent light from the sample passes;

sensor means for sensing the fluorescent light which has passed through the slit to obtain an electric signal;

signal filter means for limiting a frequency band of the electric signal from the sensor means to a frequency band predetermined depending on a width of the slit as imaged onto the sample and a speed of the scanning of the sample; and signal processing means for processing the band-limited electric signal so as to detect fluorescent substances in the sample, wherein the sample includes a plurality of colonies of microorganisms having diameters in the range of $D_1$ to $D_2$ and the frequency band of the electric signal is selected to obtain electric signals at a frequency R that corresponds to the diameter of an individual colony, where $$R = S/(W+D) \text{ (Hz)}$$

wherein S is the speed of the scanning of the sample,

W is the width of the slit as imaged onto the sample, and

D is the diameter of a colony being scanned, and the frequency range extends at least from a frequency $R_1$ for colonies of diameter $D_1$ to a frequency $R_2$ for colonies of diameter $D_2$.

2. An apparatus according to claim 1, wherein said sensor means includes a photomultiplier tube for the photoelectric conversion of the fluorescent light.

3. An apparatus according to claim 1, wherein the microorganism sample is a sample in which the microorganisms in an object to-be-inspected are caught on a membrane filter and then subjected to the fluorescent staining.

4. An apparatus for detecting microorganisms in a microorganism sample subjected to fluorescent staining, comprising:

stage means for placing thereon a microorganism sample subjected to fluorescent staining, and for transporting the sample to permit the sample to be scanned;

light source means for projecting an excitation light of a predetermined wavelength onto the sample so that a fluorescent light is originated from the sample;

slit means having a slit of a predetermined width through which the fluorescent light from the sample passes;

first optical filter means for filtering the fluorescent light from the sample to obtain a first band-limited light of a first wavelength band;

second optical filter means for filtering the fluorescent light from the sample to obtain a second hand, limited light of a second wavelength;

first sensor means for sensing the first band-limited light which has passed through the slit to obtain a first electric signal;

second sensor means for sensing the second band-limited light which has passed through the slit to obtain a second electric signal;

signal filter means for limiting a frequency band of the electric signals from the sensor means to a frequency band predetermined depending on a width of the slit as imaged onto the sample and a speed of the scanning of the sample; and processing means for processing the band-limited first and second electric signals to discriminate the microorganisms from auto-fluorescent foreign matter in the sample by utilizing a discrepancy between fluorescence spectra from the microorganisms and the auto-fluorescent foreign matter, wherein the sample includes a plurality of colonies of microorganisms having diameters in the range of $D_1$ to $D_2$, and the frequency band of the electric signals is selected to obtain electric signals at a frequency R that corresponds to the diameter of an individual colony, wherein $$R = S/(W+D) \; (Hz)$$

wherein S is the speed of the scanning of the sample,

W is the width of the slit as imaged onto the sample, and

D is the diameter of a colony being scanned, and the frequency range extends at least from a frequency $R_1$ for colonies of diameter D1 to a frequency $R_2$ for colonies of diameter $D_2$.

5. An apparatus for detecting microorganisms according to claim 4, wherein the microorganisms in the sample are caught on a membrane filter and then subjected to the fluorescent staining.

6. An apparatus for detecting microorganisms according to claim 4, wherein said first and second sensor means include a photomultiplier tube for the photoelectric conversion of the fluorescent light.

7. An apparatus for detecting microorganisms according to claim 4, wherein B excitation light having a wavelength of about 490 nm is employed as the excitation light, and two sorts of optical filters whose pass bands are respectively of 500–600 nm and 550–700 nm are employed as said first and second optical filter means.

8. An apparatus for detecting microorganisms according to claim 4, wherein V excitation light having a wavelength of about 405 nm are employed as the excitation light, and two sorts of optical filters whose pass bands are respectively at 480–530 nm and 510–560 nm are employed as said first and second optical filter means.

* * * * *